March 24, 1964 R. S. MOORE Plant Pat. 2,387
ROSE
Filed Jan. 12, 1962
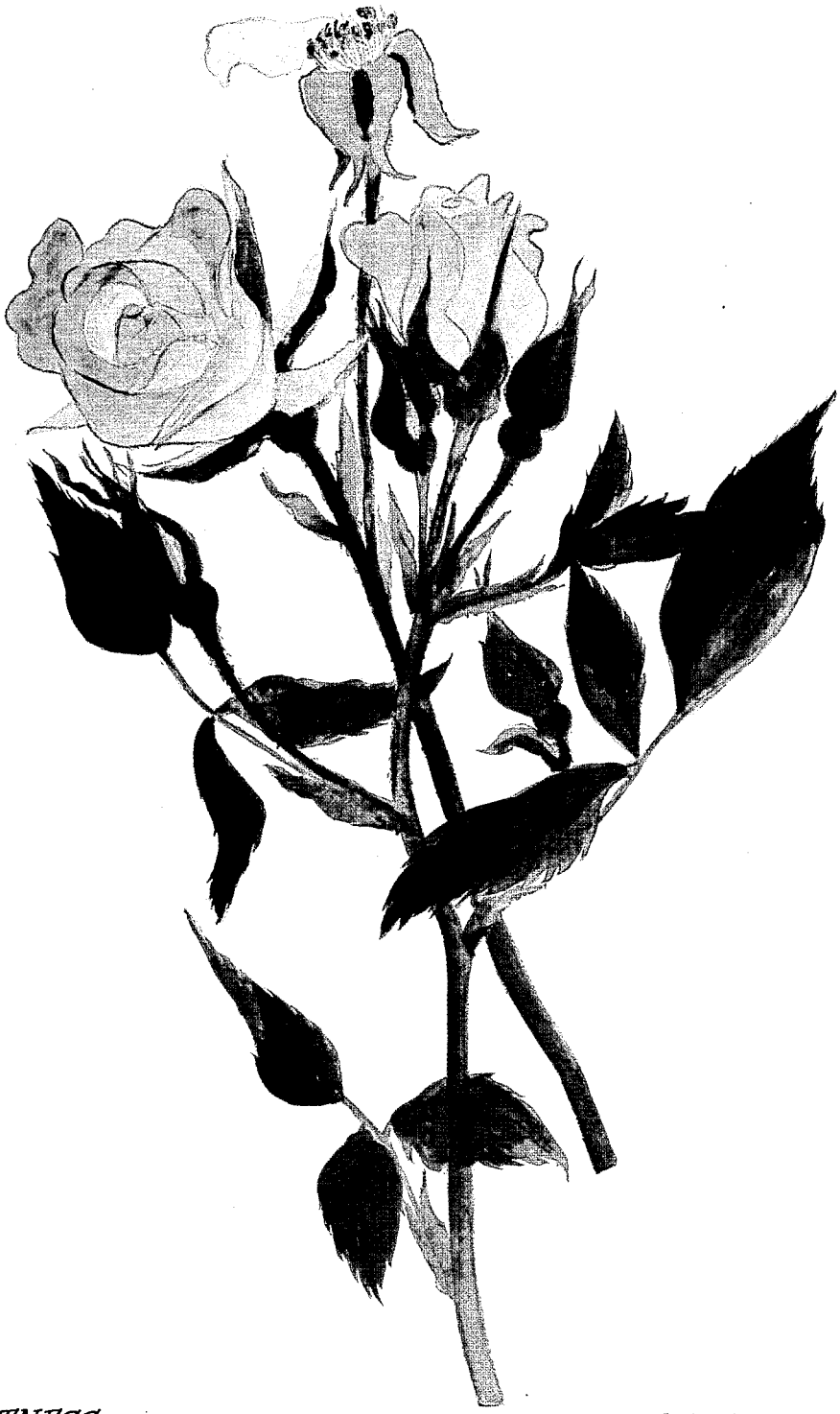
WITNESS
Jeanette Nunn Lepley
INVENTOR
RALPH S. MOORE
ATTORNEYS
Earl Jeff. & Slick United States Patent Office Plant Pat. 2,387
Patented Mar. 24, 1964

2,387
ROSE

Ralph S. Moore, 2519 E. Mineral King, Visalia, Calif.
Filed Jan. 12, 1962, Ser. No. 165,978
1 Claim. (Cl. Plt.—22)

This invention relates to a new and distinct variety of dwarf, bush-type bi-color floribunda rose plant.

This plant is characterized as to novelty by its rich green, glossy foliage and the ease with which it grows into a well-shaped, symmetrical bush or shrub.

This floribunda rose plant somewhat resembles its pollen parent, Condesa de Sastago (non-patented) in color combinations and flower shape, although the flowers are somewhat smaller and more abundant. The new and distinct variety makes a clean bushy plant for garden use and is characterized by free, vigorous growth. The flowers and buds come on stems sufficiently long for cutting and arranging. The flowers have a fruity or wild rose fragrance. If allowed to remain on the plant, the seed hips make a colorful show in the fall as they ripen.

This variety of bi-color floribunda rose plant was originated by me, in my nursery located at Visalia, California, and under conditions of careful control and observation, as a cross between an unnamed polyantha seedling (non-patented) as the seed parent and Condesa de Sastago (non-patented) as the pollen parent. Subsequent to origination of the variety, I successfully asexually reproduced it in my nursery, located as aforesaid, by budding as well as cuttings, the reproductions having run true in all respects.

The drawing illustrates the variety including foliage, buds and flowers.

Referring now specifically to the new and distinct variety of floribunda rose plant, the following is a detailed description thereof in outline; all major color plate identifications being to the British Colour Council Horticultural Colour Chart, except where common terms of color definition are employed.

Type: Dwarf; bush; half hardy; outdoor; seedling; cut flowers; garden decoration.
Class: Floribunda.

*Flowers*

Continuity: Intermittent to continuous.
Fragrance: Moderate.
Flowers borne: Three to five or more to each stem; stems are of normal strength and medium length; flowers grown in irregular, rounded clusters.
Quantity of bloom: Free, outdoors.
Bud:
*Peduncle.*—Medium length; slender; erect; medium green; numerous green hairs.
*Before calyx breaks.*—Size—medium. Form—long; pointed; without foliaceous appendages on the surface of the bud; with foliaceous parts extending beyond the tip of the bud equal to ¼ or more of its length. Color—medium green.
*As calyx breaks.*—Color—greenish yellow.
*As first petal opens.*—Size—medium. Form—pointed, ovoid. Color: outside—yellow shading to red near tip; inside—orange-red and yellow at base. Opening—opens well in all weather.
Bloom:
*Size when fully opened.*—Medium, 2½" to 2¾".
*Petalage.*—Double, with from 18 to 20 petals arranged regularly.
*Form.*—Open, cupped at first; becoming open; petals remaining at first very loosely rolled outward; becoming later, at maturity, flat cupped.
Petals: Thin; inside satiny; outside satiny.

*Shape.*—Outside—obovate; intermediate—obovate; inside—obovate.
*Color.*—Newly opened flower from plant grown outdoors (September)—Outside petal: outside surface—Straw Yellow 604 overlaid with Vermilion 18 near tip of petal; inside surface—Chinese Yellow 606 shading to Poppy Red 16, then to Vermilion 18 in upper ¼ of petal. Intermediate petal: same as outside petal. Inner petal: same as outside and intermediate petal. Rose opened for three days outdoors (September)—Outside petal: outside surface—Empire Yellow 603/1 to 603/3 at base shading or blending to Neyron Rose 623/3 (sometimes also shaded with Phlox Pink 625/3); inside surface—Empire Yellow 603/1 shading or blending into Phlox Pink 625/3 or lighter. Inside petal: both outside and inside surfaces same as outside petal.
*General color effect.*—Newly opened flower—bright orange pink with yellow base. Three days open—medium pink.
*Behavior.*—Drop off fairly cleanly; colors brighten in cool weather of spring and fall and get paler in hot summer weather.
*Flower longevity (September).*—Three to four days on bush in garden. One to two days as cut roses grown outdoors, kept at living room temperatures.
Reproductive organs:
*Stamens.*—Many; arranged regularly about pistils.
*Filaments.*—Short to medium; yellow; most with anthers.
*Anthers.*—Medium; yellow; all open at once.
*Pollen.*—Abundant; yellow.
*Pistils.*—Many.
*Styles.*—Even; short; medium; loosely separated.
*Stigma.*—Yellow.
*Ovaries.*—All enclosed in calyx.
*Hips.*—Globular; reddish; smooth; walls fleshy.
*Sepals.*—Permanent; moderately long; spear-shaped, recurved; brown.
*Seeds.*—Five to seven; medium large.

*Plant*

Foliage:
*Leaves.*—Compound of 5 leaflets; normally abundant; medium large; leathery; glossy.
*Leaflets.*—Shape—oval, lanceolate. Apex—acute. Margin—serrate. Color: mature—upper surface normal green; under surface normal green. Young—upper surface normal green; undersurface normal green tinted with red. Rachis—upper side grooved with few short hairs; under side moderately smooth with few short thorns. Stipules—medium long; medium wide with moderately short points turning out at an angle of about 45°. Disease—resistant to mildew as compared with other varieties grown under comparable cultural conditions at Visalia, California.
Growth:
*Habit.*—Dwarf; bushy; upright; many branches.
*Growth.*—Free vigorous.
*Canes.*—Medium.
*Main stems.*—Color—green. Thorns—few to several, medium and hooked downward, with long, narrow base. Prickles—few. Hairs—none.
*Branches.*—Color—bright green. Thorns—few, medium, with long, narrow base. Prickles—none to few. Hairs—none.
*New shoots.*—Color—bright green. Thorns—few, medium and hooked downward, with long, narrow base. Prickles—none to few. Hairs—none.

The following is claimed:

A new and distinct variety of floribunda rose plant, substantially as herein shown and described, of the dwarf, bush-type, outdoor variety characterized by its rich, green, glossy foliage and free, vigorous growth habits, by medium sized, satiny petals arranged regularly with newly opened flowers of bright orange pink with a yellow base and with flowers open for three days blending into medium pink, said flower resembling Condesa de Sastago in color combinations and flower shape, but with flowers somewhat smaller and more abundant.

No references cited.